United States Patent
Jeanne et al.

(10) Patent No.: US 11,449,992 B2
(45) Date of Patent: *Sep. 20, 2022

(54) METHOD AND SYSTEM FOR TELEDENTISTRY IMAGES

(71) Applicant: KONINKLIJKE PHILIPS N. V., Eindhoven (NL)

(72) Inventors: Vincent Jeanne, Migne Auxances (FR); Taylor Bevis, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 49 days.

This patent is subject to a terminal disclaimer.

(21) Appl. No.: 16/980,081

(22) PCT Filed: Mar. 25, 2019

(86) PCT No.: PCT/EP2019/057355
§ 371 (c)(1),
(2) Date: Sep. 11, 2020

(87) PCT Pub. No.: WO2019/192862
PCT Pub. Date: Oct. 10, 2019

(65) Prior Publication Data
US 2021/0019885 A1   Jan. 21, 2021

Related U.S. Application Data

(60) Provisional application No. 62/651,366, filed on Apr. 2, 2018.

(51) Int. Cl.
G06T 7/00 (2017.01)
G06T 7/90 (2017.01)
(Continued)

(52) U.S. Cl.
CPC ........ *G06T 7/0012* (2013.01); *A61B 1/00039* (2013.01); *A61B 1/04* (2013.01);
(Continued)

(58) Field of Classification Search
CPC ..... G06T 7/0012; G06T 7/90; G06T 2200/24; G06T 2207/10024; G06T 2207/30036;
(Continued)

(56) References Cited

U.S. PATENT DOCUMENTS 10,485,638 B2   11/2019   Salah
2013/0155474 A1   6/2013   Roach
(Continued)

FOREIGN PATENT DOCUMENTS

CN   104867148 A   8/2015
EP   3050512 A1   8/2016

OTHER PUBLICATIONS

Leonid Godlevsky et al: "Application of Mobile Photography With Smartphone Cameras for Monitoring of Early Caries Appearance in the Course of Orthodontic Correction Wsith Dental Brackets", Applied Medical Informatics, vol. 33, No. 4, Dec. 17, 2013, pp. 21-26.
(Continued)

*Primary Examiner* — Ali Bayat

(57) ABSTRACT

A method (300) for obtaining one or more oral images (90) using an imaging device or system (100, 200) includes: (i) obtaining (320), using an imager, an oral image; (ii) extracting (330), by a controller, one or more features from the oral image, wherein the extracted one or more features comprises at least an image quality feature and an object recognition feature; (iii) determining (340), by a decision module of the controller, whether the one or more extracted features satisfy a predetermined feature threshold; (iv) providing (350) feedback to a user regarding the obtained oral image if the
(Continued)

one or more extracted features does not satisfy the predetermined feature threshold, or authorizing (370) transmission of the oral image to a dental professional if the one or more extracted features satisfy the predetermined feature threshold; and (v) transmitting (380), if transmission is authorized, the obtained oral image to a dental professional.

12 Claims, 4 Drawing Sheets

(51) Int. Cl.
| | |
|---|---|
| *A61B 1/00* | (2006.01) |
| *A61B 1/04* | (2006.01) |
| *A61B 1/24* | (2006.01) |
| *G06V 10/56* | (2022.01) |
| *G06V 10/98* | (2022.01) |
| *G06V 20/20* | (2022.01) |

(52) U.S. Cl.
CPC .............. *A61B 1/24* (2013.01); *G06T 7/90* (2017.01); *G06V 10/56* (2022.01); *G06V 10/993* (2022.01); *G06V 20/20* (2022.01); *G06T 2200/24* (2013.01); *G06T 2207/10024* (2013.01); *G06T 2207/30036* (2013.01); *G06T 2207/30168* (2013.01)

(58) Field of Classification Search
CPC ......... G06T 2207/30168; G06T 7/0002; A61B 1/00039; A61B 1/04; A61B 1/24; G06V 10/56; G06V 10/993; G06V 20/20; G06V 10/44; G06V 2201/03; A61C 9/0046; A61C 7/002; G06K 9/6253
USPC ........................................................ 382/128
See application file for complete search history.

(56) References Cited

U.S. PATENT DOCUMENTS

| | | | |
|---|---|---|---|
| 2018/0028064 A1* | 2/2018 | Elbaz | A61C 1/088 |
| 2018/0028294 A1 | 2/2018 | Vernikov | |
| 2018/0263731 A1* | 9/2018 | Pokotilov | G06T 17/20 |
| 2020/0000552 A1* | 1/2020 | Mednikov | G16H 30/40 |
| 2021/0068923 A1* | 3/2021 | Carrier, Jr. | A61C 7/002 |
| 2021/0393375 A1* | 12/2021 | Chekh | G06T 19/20 |

OTHER PUBLICATIONS

Mohamed Estai et al: "Comparison of a Smartphone-Based Photographic Method With Face-To-Face Caries Assessment" A Mobile Teledentistry Model, Telemedicine and E-Health, vol. 23, No. 5, May 31, 2017, pp. 435-440.
International Search Report dated Jun. 26, 2019.

* cited by examiner

Reject:
Image capture doesn't show requested teeth

Prompt retake:

Approve

METHOD AND SYSTEM FOR TELEDENTISTRY IMAGES

CROSS-REFERENCE TO PRIOR APPLICATIONS

This application is the U.S. National Phase application under 35 U.S.C. § 371 of International Application No. PCT/EP2019/057355, filed on Mar. 25, 2019, which claims the benefit of U.S. Provisional Application No. 62/651,366, filed on Apr. 2, 2018. These applications are hereby incorporated by reference herein.

FIELD OF THE INVENTION

The present disclosure is directed generally to methods and systems for obtaining high-quality oral images for teledentistry.

BACKGROUND

Individuals are generally instructed to undergo oral checkups at least twice a year to ensure proper oral care, and many dental insurance programs provide coverage for these oral checkups. Between checkups there may be situations where an individual or an oral care professional desires a review of their oral health, including an indication that the condition of their oral health has or has not adversely changed.

Teledentistry, which is the transfer of dentistry information such as clinical information and/or oral images over a telecommunications system, offers a system for oral review or analysis between in-person checkups. Teledentistry is a rapidly growing service as it offers a low-cost and low-burden solution utilizing technology, namely smartphones or other cameras, to which individuals readily have access. On-demand dental care has the potential to provide consumers with greater peace of mind and expedited treatment when an intervention from a dental professional is required. Furthermore, teledentistry can lower the cost of dental services, and can improve access to and delivery of dental services. Indeed, in some situations, teledentistry may be a replacement for an in-person checkup.

Teledentistry necessarily requires dental images obtained by an individual. The utility of an image for assessing oral health is determined by many features, including whether the image properly contains the target teeth, the clarity of the image, the lighting within the environment, and/or the viewing angle, among others. An image may be determined to be of high-quality when the details in the image facilitate understanding of the patient's oral health by a professional. Typically, to ensure high-quality images, multiple images of the same individual must be taken in numerous predetermined angles. These multiple files must then be transmitted to the dental professional for assessment. Invariably, some or all of the images are unusable due to failure to capture target teeth or regions of the mouth, poor clarity, poor lighting, improper angles, and/or many other reasons. It is common, therefore, for dental professionals to either use inferior images in an analysis, or to request additional images from the individual. Both scenarios are inefficient, expensive, and potentially delay treatment.

Accordingly, there is a continued need in the art for teledentistry systems and methods that ensure capture and transmission of high-quality oral images.

SUMMARY OF THE INVENTION

The present disclosure is directed to inventive methods and systems for obtaining high-quality oral images. Various embodiments and implementations herein are directed to an imaging system configured to identify high-quality oral images. The imaging system comprises an imager configured to obtain one or more images of the mouth. A processor extracts one or more features from the oral images, including features related to image quality and features related to object recognition. The processor analyzes the extracted features to determine whether they satisfy a predetermined feature threshold. If the extracted features do not satisfy the predetermined feature threshold, the system provides feedback to the user regarding the one or more images, which enables the user to obtain new images of higher quality. If the extracted features do satisfy the predetermined feature threshold, the one or more images are transmitted to a dental professional where they can be utilized for analysis by the professional.

Generally in one aspect, a method for obtaining one or more oral images using an imaging device or system is provided. The method includes: (i) obtaining, using an imager of the imaging device or system, an oral image; (ii) extracting, by a controller of the imaging device or system, one or more features from the obtained oral image, wherein the extracted one or more features comprises at least an image quality feature and an object recognition feature; (iii) determining, by a decision module, whether the one or more extracted features satisfy a predetermined feature threshold; (iv) providing, via a user interface of the imaging device or system, feedback to a user regarding the obtained oral image if the one or more extracted features does not satisfy the predetermined feature threshold, or authorizing transmission of the obtained oral image to a dental professional if the one or more extracted features satisfy the predetermined feature threshold; and (v) transmitting, if transmission is authorized, the obtained oral image to a dental professional.

According to an embodiment, the step of providing feedback to a user comprises instructions for a desired image.

According to an embodiment, the imaging device or system is configured to direct the user to obtain a new oral image if the one or more extracted features do not satisfy the predetermined feature threshold.

According to an embodiment, one or more imaging sensor parameters are controlled or determined by image properties at one or more points within an obtained oral image.

According to an embodiment, the image quality feature comprises blur quantification, specular highlight quantification, and/or dynamic range detection.

According to an embodiment, the object recognition feature comprises output filtering using a template, and/or characterization of a presence or absence of an oral feature using a trained detector.

According to an embodiment, the decision module comprises one or more of a color detection algorithm, a Canny edge detection algorithm, a Deriche edge detection algorithm, a Sobel operator or filter, a Harris corner detection algorithm, a Gaussian filter, a Hessian matrix, and a local binary pattern algorithm.

According to an embodiment, the imaging device or system is a smartphone and the imager is a smartphone camera.

According to an aspect is an imaging device configured to obtain one or more high-quality oral images. The device includes: an imager configured to obtain one or more images; a user interface configured to provide feedback to a user of the imaging device; a communications module configured to transmit one or more oral images; and a controller configured to: (i) extract one or more features from the obtained oral image, wherein the extracted one or more features comprises at least an image quality feature and an object recognition feature; (ii) determine, by a decision module, whether the one or more extracted features satisfy a predetermined feature threshold; (iii) provide, via the user interface of the imaging device or system, feedback to a user regarding the obtained oral image if the one or more extracted features does not satisfy the predetermined feature threshold, or authorize transmission of the obtained oral image to a dental professional if the one or more extracted features satisfy the predetermined feature threshold; and (iv) direct the communications module to transmit, if transmission is authorized, the obtained oral image to a dental professional.

According to an aspect is an imaging system configured to obtain one or more high-quality oral images. The system includes: an imaging device comprising an imager configured to obtain one or more images, and a communications module configured to transmit one or more oral images; a processing device comprising: a communications module configured to receive one or more oral images from the imaging device; and a controller configured to: (i) extract one or more features from the received oral image, wherein the extracted one or more features comprises at least an image quality feature and an object recognition feature; (ii) determine, by a decision module, whether the one or more extracted features satisfy a predetermined feature threshold; (iii) provide, via a user interface, feedback to a user regarding the obtained oral image if the one or more extracted features does not satisfy the predetermined feature threshold, or authorize transmission of the obtained oral image to a dental professional if the one or more extracted features satisfy the predetermined feature threshold; and (iv) direct the communications module to transmit, if transmission is authorized, the obtained oral image to a dental professional.

As used herein for purposes of the present disclosure, the term "controller" is used generally to describe various apparatus relating to the operation of an imaging apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and device for teledentistry. More generally, Applicant has recognized and appreciated that it would be beneficial to provide a system to ensure that high-quality oral images are obtained by an individual. Accordingly, the methods described or otherwise envisioned herein provide an imaging device or system such as a smartphone, smart mirror, and/or other imaging device configured to obtain one or more images of the individual's dental region. The imaging device or system includes a processor configured to extract one or more features from the oral images, including features related to image quality and features related to object recognition. The processor analyzes the extracted features to determine whether they satisfy a predetermined feature threshold. If the extracted features do not satisfy the predetermined feature threshold, the system provides feedback to the user regarding the one or more images, which enables the user to obtain new images of higher quality. If the extracted features do satisfy the predetermined feature threshold, the one or more images are transmitted to a dental professional where they can be utilized for analysis by the professional.

Figure 1:
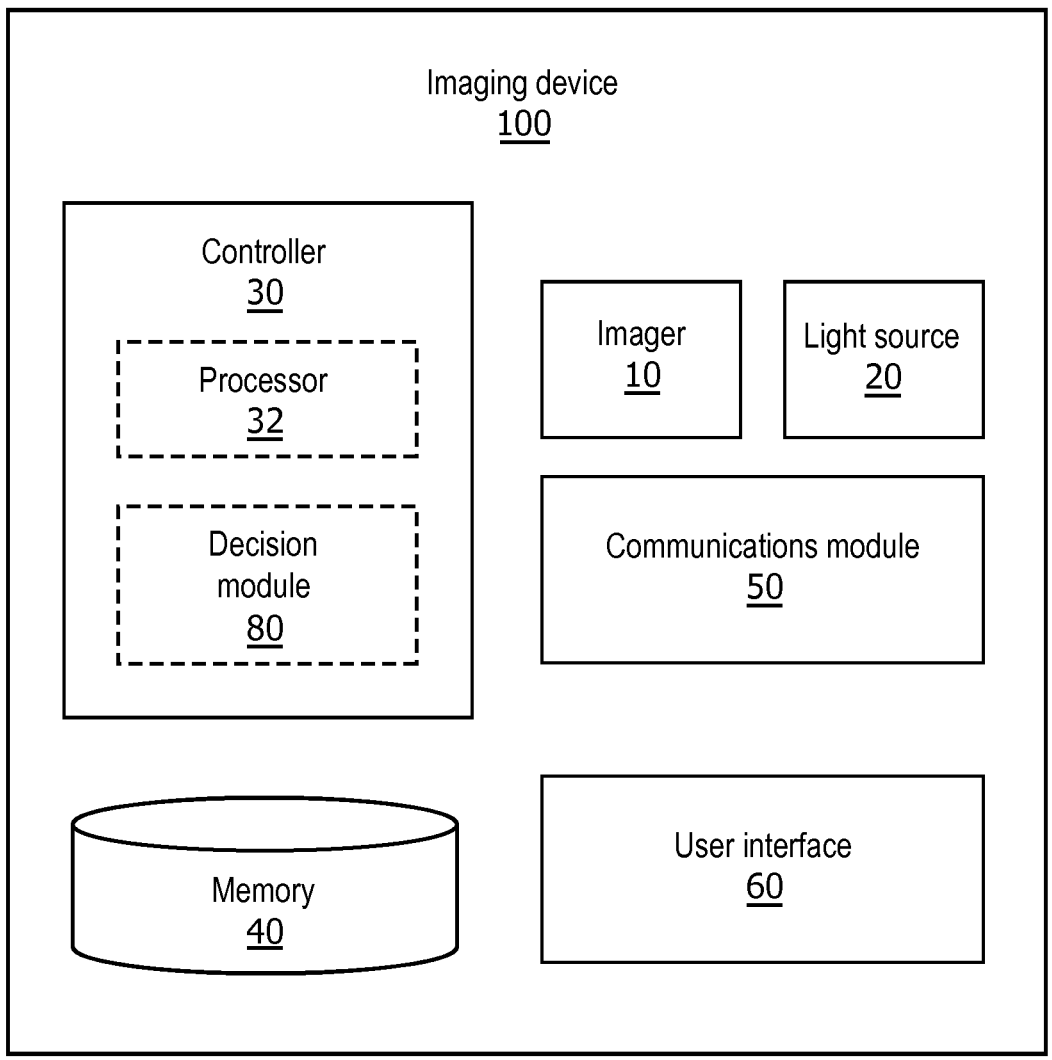
FIG. 1 is a schematic representation of an imaging device, in accordance with an embodiment.

Referring to FIG. 1, in one embodiment, is an imaging device 100 configured to obtain images from a user's mouth. Imaging device 100 may be any device with an imager capable of obtain oral images, preferably in a digital format. For example, imaging device 100 may be a smartphone, smart mirror, wearable computing device, digital camera, laptop, and/or any other computing device or capture device capable of capturing images. The imaging device 100 may optionally comprise software such as an application which facilitates one or more aspects of the imaging system or method as described or otherwise envisioned herein.

Imaging device 100 comprises an imager 10 configured to obtain images from a user's mouth. Imager 10 is an image sensor such as a CCD or CMOS sensor, among others. For example, imager 10 may be a standalone digital camera, or may be a camera integrated into an oral care device, a smartphone, a smart mirror, a wearable device, and/or any other computing or image capture device. The imaging device 100 or imager 10 may comprise or otherwise be in communication with a light source 20 configured to illuminate one or more regions of the mouth. For example, light source 20 may be a flash or other light source associated with the device 100 or system. Light source 20 can be or comprise any light source, such as an LED light source, that emits light capable of facilitating high-quality oral imaging. According to an embodiment, the light source may comprise light from two or more light sources. The imager 10 and/or light source 20 may be configured to operate periodically, continuously, and/or in response to a stimulus. For example, the imager 10 and light source 20 can obtain an image in response to a user taking an image, or in response to a user positioning the imager over a portion of the oral cavity, as detected by the imager in real-time.

Imaging device 100 further comprises a controller 30 configured to receive the one or more images obtained from the imager 10. Controller 30 may be formed of one or multiple modules, and can configured to operate the imager 10 in response to an input, such as input obtained via a user interface. Controller 30 can comprise, for example, at least a processor 32. The processor 32 may take any suitable form, including but not limited to a microcontroller, multiple microcontrollers, circuitry, a single processor, or plural processors. Controller 30 and/or imaging device 100 may also comprise a memory 40. The memory 40 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of imaging device 100.

Imaging device 100 further comprises a communications module 50 configured to receive and/or transmit information via a wired and/or wireless communications network. The communications module 50 can be any module, device, or means capable of transmitting a wired or wireless signal, including but not limited to a Wi-Fi, Bluetooth, near field communication, and/or cellular module. The communications module 50 can, for example, transmit one or more images obtained by the imager.

According to an embodiment, imaging device 100 includes a user interface 60 configured to provide information to a user and/or receive information from a user. The user interface 60 can take many different forms, but is configured to provide information to the user and/or receive information from the user. For example, the information can be read, viewed, heard, felt, and/or otherwise interpreted. Accordingly, the user interface may be a display that provides information to the user, a haptic mechanism that provides haptic feedback to the user, a speaker to provide sounds or words to the user, a simple LED light or array of LEDs, or any of a variety of other user interface mechanisms. According to an embodiment, the user interface 60 provides feedback to a user as images are obtained or after images are obtained. For example, user interface 60 can notify a user when an image is not of sufficient quality as determined by the methods described or otherwise envisioned herein. User interface 60 can also provide instructions or guidance to the user about images to obtain, or about improving images, among many other types of information and guidance.

Figure 2:
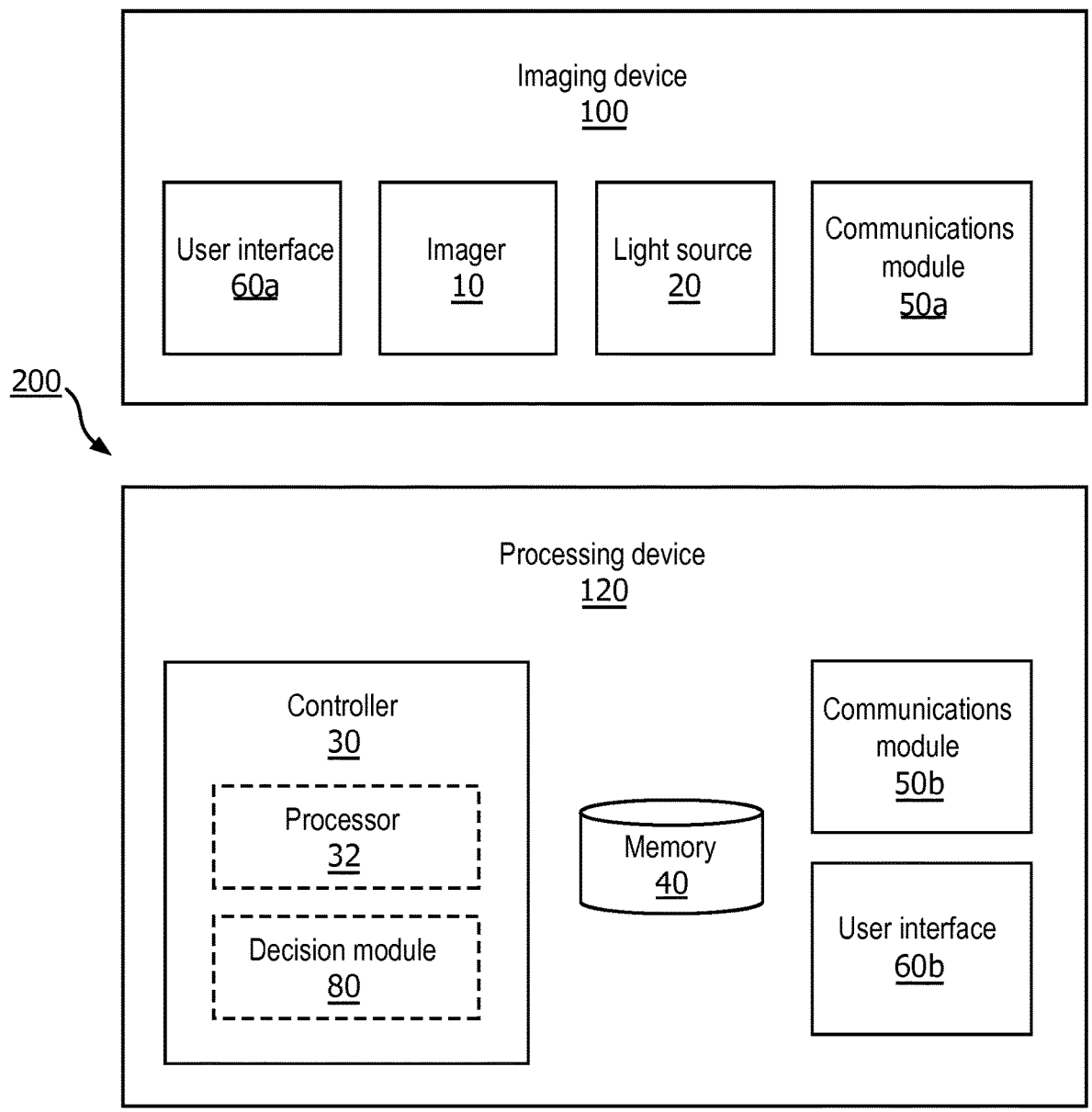
FIG. 2 is a schematic representation of an imaging system, in accordance with an embodiment.

Referring to FIG. 2, in one embodiment, is an imaging system 200 configured to obtain high-quality images from a user's mouth. According to this embodiment, imaging system 200 comprises an imaging device 100 and a processing device 120. Imaging device 100 is configured to obtain one or more images of the user's mouth, and to transmit those images to the processing device 120 which may be locally or remotely located, or even be part of the imaging device 100. Processing device 120 is configured to receive and analyze the one or more images received from the imaging device, and to transmit high-quality images, where quality is determined by the methods described or otherwise envisioned herein, to a dental professional.

Imaging device 100 can be any device with an imager capable of obtain oral images, preferably in a digital format. For example, imaging device 100 may be a smartphone, smart mirror, wearable computing device, digital camera, laptop, and/or any other computing device or capture device capable of capturing images. The imaging device 100 may optionally comprise software such as an application which facilitates one or more aspects of the imaging system or method as described or otherwise envisioned herein. Imaging device 100 comprises an imager 10, such as a CCD or CMOS sensor, among others, configured to obtain images from a user's mouth. Imaging device 100 may be a stand-alone digital camera, or may be a camera integrated into an oral care device, a smartphone, a smart mirror, a wearable device, and/or any other computing device. Imaging device 100 may comprise a light source 20 configured to illuminate one or more regions of the mouth. The device may also comprise a user interface.

The imaging device 100 also comprises a communications module 50*a* configured to receive and/or transmit information via a wired and/or wireless communications network. The communications module 50*a* can be any module, device, or means capable of transmitting a wired or wireless signal, including but not limited to a Wi-Fi, Bluetooth, near field communication, and/or cellular module. The communications module 50*a* can, for example, transmit one or more images obtained by the imager to the processing device 120.

According to an embodiment, imaging device 100 also includes a user interface 60*a*, such as user interface 60 as described previously herein, configured to provide information to a user and/or receive information from a user. The user interface 60*a* can take many different forms, and is configured to provide information to the user and/or receive information from the user. According to an embodiment, the user interface 60*a* provides feedback to a user as images are obtained or after images are obtained. For example, user interface 60*a* can notify a user when an image is not of sufficient quality as determined by the methods described or otherwise envisioned herein. User interface 60*a* can also provide instructions or guidance to the user about images to obtain, or about improving imaging, among many other types of information and guidance.

Processing device 120 can be any device configured to receive images from the imaging device 100. For example, processing device 120 may be a smartphone, smart mirror, wearable computing device, laptop, and/or any other computing device. Processing device 120 may optionally comprise software such as an application which facilitates one or more aspects of the imaging system or method as described or otherwise envisioned herein.

Processing device 120 comprises a controller 30 configured to receive the one or more images obtained from the imager. Controller 30 may be formed of one or multiple modules, and can comprise, for example, processor 32. The processor 32 may take any suitable form, including but not limited to a microcontroller, multiple microcontrollers, circuitry, a single processor, or plural processors. Processing device 120 may comprise a memory 40, which can take any suitable form, including a non-volatile memory and/or RAM. The memory 40 can be configured to store one or more received images or any other information or instructions.

The processing device further comprises a communications module 50b configured to receive and/or transmit information via a wired and/or wireless communications network, including information transmitted from communications module 50a of the imaging device 100. The communications module 50b can be any module, device, or means capable of transmitting a wired or wireless signal, including but not limited to a Wi-Fi, Bluetooth, near field communication, and/or cellular module.

According to an embodiment, processing device 120 includes a user interface 60b configured to provide information to a user and/or receive information from a user. The user interface 60b can take many different forms, and is configured to provide information to the user and/or receive information from the user. According to an embodiment, the user interface 60b provides feedback to a user as images are obtained or after images are obtained. For example, user interface 60b can notify a user when an image is not of sufficient quality as determined by the methods described or otherwise envisioned herein. User interface 60b can also provide instructions or guidance to the user about images to obtain, or about improving imaging, among many other types of information and guidance.

Figure 3:
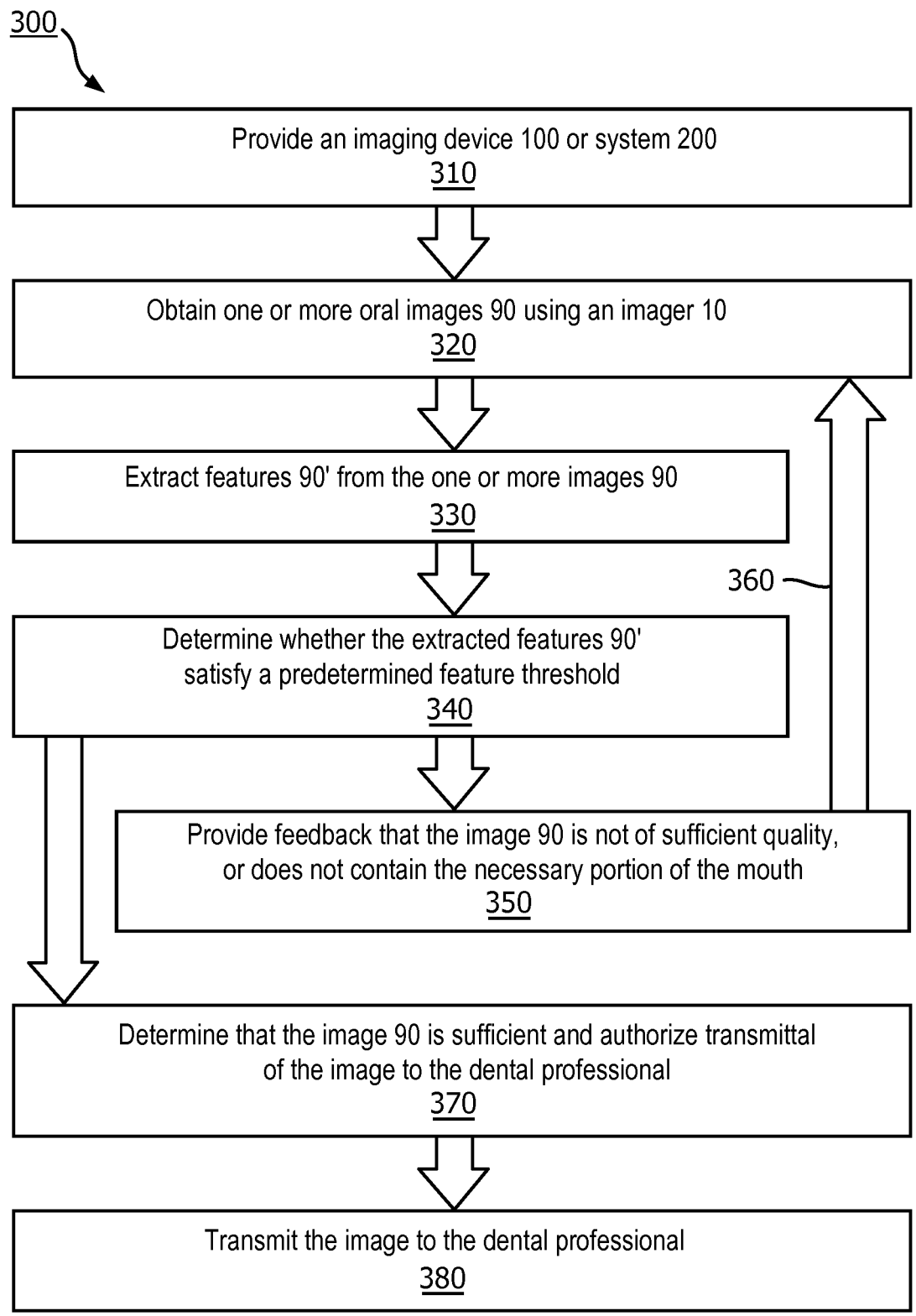
FIG. 3 is a flowchart of a method for obtaining a high-quality dental image, in accordance with an embodiment.

Referring to FIG. 3, in one embodiment, is a flowchart of a method 300 for obtaining high-quality images 90 from a user's mouth. At step 310, an imaging system is provided. The imaging system may be any of the imaging systems described or otherwise envisioned herein. For example, the imaging system may be imaging device 100 or imaging system 200, among many other devices or systems. Generally, the imaging system will comprise an imager 10 configured to obtain one or more images 90 of a user's mouth, a controller 30 configured to receive and analyze the obtained one or more images, a communications module 50 configured to transmit and/or receive information over a wired and/or wireless communications system, and a user interface 60 to receive information from a user and/or provide information to a user. Although method 300 is described within the framework of imaging device 100 and imaging system 200, the method can be implemented using any other appropriately configured imaging device or system as described or otherwise envisioned herein.

At step 320 of the method, one or more images 90 of the user's mouth are obtained using imager 10 of the imaging device 100. According to a preferred embodiment the imager is a 2D imaging sensor integrated into a smart connected medium such as a smartphone, laptop, or other connected camera that enables the capture of wavelengths in the visible part of the spectrum. In an optional embodiment, the acquisition of wavelengths can include near- to mid-infrared wavelengths using imaging sensors sensitive in the relevant parts of the light spectrum.

According to an embodiment, one or more imaging sensor parameters are controlled or determined by image properties at predetermined key points within an obtained image 90, which can be either preprogrammed or detected. For example, the camera's automatic white balance can be set based on the average properties of the color level identified on teeth areas, which can be detected either by means of an image overlay that the user manually aligns to or by detecting teeth using color properties in a heuristic or machine learning fashion. In another embodiment, the camera exposure is determined only by the pixel properties contained within a specific key area, such as the inside of the user's mouth, rather than the entire field of view of the image. This specific control ensures that the image capture is solely focused on providing the best sensor settings for the area of interest only. Thus, areas of the mouth, cheek, body, or background that are not desired are deemed irrelevant for further analysis by a dental professional.

According to an embodiment, image capture comprises capturing one or multiple images. For example, the system may obtain a series of images, such as the 'live' photo as enabled by Apple iOS, to allow either: (i) the system to automatically select the best image according to the criteria set forth in or by the decision module; or (ii) the dental professional to select the most appropriate image or images from the series for analysis.

According to an embodiment, the user may wish to obtain images to share with a dental professional, either in response to injury, pain, or other stimulus, or as part of a scheduled checkup or other routine maintenance or care. The user may receive a notification or other stimulus to obtain the one or more images. Imaging device 100 may comprise software such as an app that provides a notification to a user that images are required. For example, imaging device 100 may be a smartphone with an app installed that provides notifications to obtain routine images. Alternatively, the user may instigate a teledentistry session by accessing software or an online website or service and will be prompted to obtain one or more images. Accordingly, imaging device 100 may receive instructions about which images to obtain for the session, and these instructions may be prompted, in whole or in part, based on information from the user and/or the dental professional. For example, the user may be prompted to obtain images at a specific angle, or to include certain teeth in the field of view, among many other possible prompts.

The images obtained by the user via the imager may be of any portion of the user's mouth, including but not limited to gums, teeth, tongue, or any other part of the oral cavity. The images may be analyzed immediately or may be stored for batch processing in real-time or near real-time. The images may be retained by the device for analysis, or may be transmitted to another device for downstream analysis as described or otherwise envisioned herein. The images 90 are transmitted to and/or received by controller 30 for feature extraction and analysis.

At step 330 of the method, controller 30 extracts one or more features 90' from the obtained one or more oral images 90. According to an embodiment, controller 30 extracts at least two sets of features from the one or more images, including at an image quality feature and an object recognition feature, although many other feature types are possible.

According to an embodiment, controller 30 extracts one or more image quality features 90', which targets characterization of the impact a user has on the image acquisition process. The image quality feature 90' can include, for example, blur quantification using discrete wavelet transform or frequency analysis to quantify the amount of high frequency components available in the region of interest within an image. As another example, the image quality feature 90' may include specular highlight quantification using either detection of 'hotspots' using thresholding and/or a Gaussian filter. As another example, the image quality feature 90' may include dynamic range detection by computing the available distribution of color in each channel over the region of interest. The image quality feature 90' may include other image quality features in addition to those described herein.

According to an embodiment, controller 30 extracts an image content feature, which targets characterization of the impact the image sensor has on the image acquisition process. The image content feature can include, for example, filtering of the output using a dedicated template. Since each image is expected to represent a specific portion of the mouth related to a diagnostic process, correlating the captured image with a predetermined template will provide a metric characterizing how alike the captured image and targets are. The process may utilize Haar-like features, color-based features, or other features. As another example, the image content feature can comprise, utilize, or by analyzed by a trained detector. Since each image is expected to contain a specific portion of the mouth such as teeth or gums, trained detectors which can optional utilize machine learning algorithms can provide a metric characterizing the presence or absence of such key mouth parts essential to the analysis performed by the dental professional. The image quality feature may include other image content features in addition to those described herein.

According to an embodiment, the features can be extracted or analyzed using any feature extraction method, algorithm, or filter. For example, the feature extraction method, algorithm, or filter may comprise color detection, Canny edge detection, Deriche edge detection, a Sobel operator or filter, Harris corner detection, Gaussian filters, blob detection based on the Laplacian of the Gaussian, a Hessian matrix, local binary patterns, and/or any other feature extraction method, algorithm, or filter.

Once extracted, the one or more features can be analyzed in real-time or near real-time, or can be stored for subsequent analysis. For example, the extracted one or more features can be stored in memory 40, and extracted features can be associated in memory with the image 90 or images from which they were obtained.

At step 340 of the method, the imaging system 200 determines whether the one or more extracted features satisfy a predetermined feature threshold. According to an embodiment, the imaging device or system comprises a Decision Module 80 which is configured to analyze the one or more extracted features. Decision Module 80 effectively gates the transmission of image data to the dental professional. If the image quality is poor and/or doesn't contain the requested features, feedback will be provided to the user. If the image quality is sufficiently high and/or contains the requested features, the image can be transmitted to the dental professional.

Decision Module 80 may be programmed or configured, for example, to compare the one or more extracted features 90' to a predetermined feature threshold to determine whether the image is of sufficient quality to deem it a high-quality image that may be transmitted to and/or utilized by a dental professional. An image will either be accepted or rejected based on the comparison. According to an embodiment, Decision Module 80 is programmed or configured to analyze the one or more extracted features 90' using a heuristic model or function. According to another embodiment, Decision Module 80 is programmed or configured to analyze the one or more extracted features using a classification system such as a decision tree, a naive Bayes classifier, a support vector machine, or similar classifier or algorithm. According to another embodiment, Decision Module 80 is programmed or configured to analyze the one or more extracted features using machine learning and/or artificial intelligence such as neural networks and/or ensemble methods.

At step 350 of the method, Decision Module 80 determines, if the one or more extracted features 90' do not satisfy the predetermined feature threshold in step 340, that the image obtained by the user is insufficient and provides feedback to the user to obtain a replacement image. The feedback can be provided via the user feedback, or via any other mechanism. For example, the user can receive a visual, haptic, audible, or other notification that the image is insufficient. The image may be insufficient, for example, if the image quality is poor and/or doesn't contain the desired or requested portion of the mouth.

Figure 4:
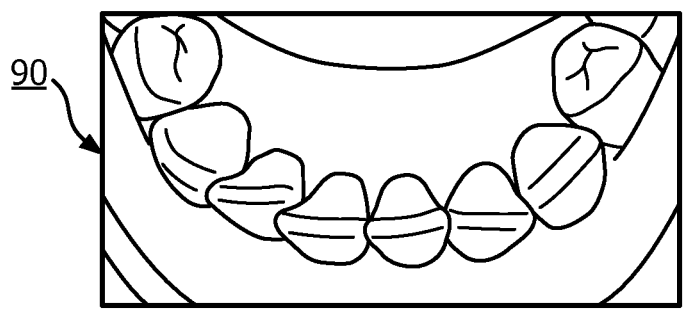
FIG. 4 is a schematic representation of feedback provided to a user of an imaging device or system, in accordance with an embodiment.
Figure 4:
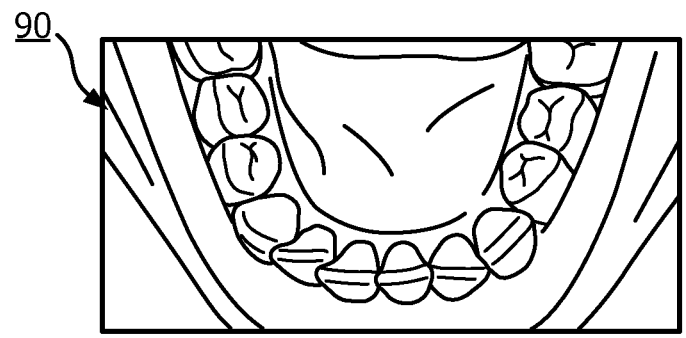

Referring to FIG. 4, for example, in the top panel the image obtained by the user is blurry and/or doesn't contain the proper portion of the mouth. Accordingly, at step 340 of the method, the Decision Module 80 determines that the one or more extracted features 90' do not satisfy the predetermined feature threshold. At step 350, the imaging system provides feedback to the user that the "capture doesn't show the requested teeth," and prompts the user to obtain a new image preferably containing the requested portion of the mouth. Many other methods of providing feedback to the user are possible.

At step 360 of the method, if the image does not satisfy the predetermined threshold, the user returns to step 320 to obtain an additional one or more images using the imager. Step 360 may comprise feedback or instructions from the system or device to the user regarding the image that was obtained and/or the desired image. Alternatively, the imaging system analyzes a second image that was previously obtained, typically of the same location, and repeats the analysis to determine whether the second image satisfies the predetermined feature threshold in step 340. This can be repeated an unlimited number of times.

Alternatively, at step 370 of the method, Decision Module 80 determines, if the one or more extracted features satisfy the predetermined feature threshold in step 340, that the image obtained by the user is of sufficiently high quality and/or contains the desired or requested portion of the mouth. Accordingly, the imaging system can then authorize or initiate transmission of the obtained oral image to a dental professional. This prevents wasted time or inferior diagnosis due to poor images, which is an ongoing issue in current embodiments of teledentistry.

Accordingly, at step 380 of the method, images determined to be of sufficiently high quality and/or containing the desired or requested portion of the mouth can be transmitted to the dental professional or a service utilized by the dental professional in real-time as images are authorized, or only after a predetermined number or quality of images are obtained. Images can be transmitted to the dental professional or other third-party system or service via wired and/or wireless communication using a communications module 50 of the imaging device or system. The system may be configured or designed to only transmit images to a dental professional or other third-party system or service if a requested number of images of sufficiently high quality are obtained, and/or if certain regions are captured in images of sufficiently high quality. For example, the system may be configured to require images of sufficiently high quality of both the top and bottom teeth, or of front and back teeth, or of a certain tooth, before it will authorize transmission of the images to the dental professional or other third-party system or service.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for obtaining one or more oral images using an imaging device or system, the method comprising:
   obtaining, using an image sensor of the imaging device or system, an oral image;
   extracting, by a controller of the imaging device or system, one or more features from the obtained oral image, wherein the extracted one or more features comprises at least an image quality feature and an object recognition feature, wherein the object recognition feature comprises an outcome of output filtering using a template, and/or characterization of a presence or absence of an oral feature using a trained detector;
   determining, by a decision module, whether the one or more extracted features satisfy a predetermined feature threshold;
   providing, via a user interface of the imaging device or system, feedback to a user regarding the obtained oral image if the one or more extracted features does not satisfy the predetermined feature threshold, or authorizing transmission of the obtained oral image to a dental professional if the one or more extracted features satisfy the predetermined feature threshold; and
   transmitting, if transmission is authorized, the obtained oral image to a dental professional.

2. The method of claim 1, wherein the step of providing feedback to a user comprises providing instructions to the user for obtaining an image having features that satisfy the predetermined feature threshold.

3. The method of claim 1, wherein the imaging device or system is configured to direct the user to obtain a new oral image if the one or more extracted features does not satisfy the predetermined feature threshold.

4. The method of claim 1, wherein one or more image parameters are controlled or determined by image properties at one or more points within the obtained oral image.

5. The method of claim 1, wherein the image quality feature comprises blur quantification, specular highlight quantification, and/or dynamic range detection.

6. The method of claim 1, wherein the decision module is configured to analyze the one or more extracted features using one or more of a color detection algorithm, a Canny edge detection algorithm, a Deriche edge detection algorithm, a Sobel operator or filter, a Harris corner detection algorithm, a Gaussian filter, a Hessian matrix, and a local binary pattern algorithm.

7. The method of claim 1, wherein the imaging device or system is a smartphone and the image sensor is a smartphone camera.

8. An imaging device configured to obtain one or more high-quality oral images (90), comprising:
- an image sensor configured to obtain one or more images;
- a user interface configured to provide feedback to a user of the imaging device;
- a communications module configured to transmit one or more oral images; and
- a controller configured to: (i) extract one or more features from the obtained oral image, wherein the extracted one or more features comprises at least an image quality feature and an object recognition feature, wherein the image quality feature comprises blur quantification, specular highlight quantification, and/or dynamic range detection; (ii) determine, by a decision module, whether the one or more extracted features satisfy a predetermined feature threshold; (iii) provide, via the user interface of the imaging device or system, feedback to a user regarding the obtained oral image if the one or more extracted features does not satisfy the predetermined feature threshold, or authorize transmission of the obtained oral image to a dental professional if the one or more extracted features satisfy the predetermined feature threshold; and (iv) direct the communications module to transmit, if transmission is authorized, the obtained oral image to a dental professional.

9. The imaging device of claim 8, wherein the object recognition feature comprises the outcome of output filtering using a template, and/or characterization of a presence or absence of an oral feature using a trained detector.

10. The imaging device of claim 8, wherein the imaging device or system is a smartphone and the image sensor is a smartphone camera.

11. An imaging system configured to obtain one or more high-quality oral images, comprising:
- an imaging device comprising an image sensor configured to obtain one or more oral images, and a communications module configured to transmit one or more oral images; and
- a processing device comprising: a communications module configured to receive one or more oral images from the imaging device; and a controller configured to: (i) extract one or more features from the received oral image, wherein the extracted one or more features comprises at least an image quality feature and an object recognition feature, wherein the object recognition feature comprises the outcome of output filtering using a template, and/or characterization of a presence or absence of an oral feature using a trained detector; (ii) determine, by a decision module, whether the one or more extracted features satisfy a predetermined feature threshold; (iii) provide, via a user interface, feedback to a user regarding the obtained oral image if the one or more extracted features does not satisfy the predetermined feature threshold, or authorize transmission of the obtained oral image to a dental professional if the one or more extracted features satisfy the predetermined feature threshold; and (iv) direct the communications module to transmit, if transmission is authorized, the obtained oral image to a dental professional.

12. The imaging system of claim 11, wherein the image quality feature comprises blur quantification, specular highlight quantification, and/or dynamic range detection.

* * * * *